United States Patent [19]
Zelaskowski

[11] 3,934,976

[45] Jan. 27, 1976

[54] TRACE LEAD ANALYSIS METHOD

[75] Inventor: Catherine A. Zelaskowski, Trenton, N.J.

[73] Assignee: Mobil Oil Corporation, New York, N.Y.

[22] Filed: Feb. 19, 1974

[21] Appl. No.: 443,545

[52] U.S. Cl. ........ 23/230 R; 23/230 HC; 23/230 M
[51] Int. Cl.² ................. G01N 31/22; G01N 33/20; G01N 33/22
[58] Field of Search........ 23/230 R, 230 M, 230 HC

[56] References Cited
UNITED STATES PATENTS 3,806,319  4/1974  Fabbro et al. .................. 23/230 R

OTHER PUBLICATIONS

Daniels et al., Physical Chemistry, Third Edition, p. 621, (1966), John Wiley & sons Inc., N.Y.

Pollard et al., "4-(2 Pyridylazo)-Resorcinol Asa Possible Analytical Reagent for the Colorimetric Est. of Cobatt, Lead, and Uranium." 20 Anal. Chim. Acta 26-31, 1959.

Mapstone, "A Qualitative Test for Tel in Gasoline," 42 Journal Inst. petrol. 67, 1956.

Webster's 3d New Int'l Dictionary, unabridged, p. 333, 1966.

Primary Examiner—Morris O. Wolk
Assistant Examiner—Barry I. Hollander
Attorney, Agent, or Firm—Charles A. Huggett; Raymond W. Barclay; Stanley A. Strober

[57] ABSTRACT

The lead content of gasolines, particularly in concentrations of from 0.00 to 0.10 gram of lead per U.S. gallon of gasoline, is determined colorimetrically by mixing iodine and tetraorganoammonium halide solution with the gasoline, subjecting the mixture to ultraviolet light or heat, agiating the mixture with ammonium nitrate or nitric acid, passing the aqueous phase into 4-(2-pyridylazo)-resorcinol disodium and comparing the resulting color with a standard color scale or a colorimeter to determine the initial lead concentration.

9 Claims, No Drawings

TRACE LEAD ANALYSIS METHOD

BACKGROUND OF THE INVENTION

1. Field of the Invention

This invention relates to a trace lead analysis method, and in particular to a method of analyzing gasoline containing trace amounts of organolead or inorganic lead compounds.

2. Description of the Prior Art

The availability of unleaded gasoline to modern motorists is a subject of increased industrial effort among gasoline suppliers. The marketing operations for unleaded gasoline, however, involve shipment over present distributive facilities which also carry leaded gasoline. Accordingly, lead is still present in pipelines, tank cars, tank trucks, in service station pumps and reservoirs and the like. Coupled with this is a prospective governmental fine which may be exacted for failure of the gasoline supplier to keep the lead content in unleaded gasoline below a certain maximum, such as 0.05 grams per gallon. Accordingly, it would be advantageous to make rapid on-the-spot analyses of gasoline samples for lead which may have been picked up during shipment of the gasoline and to permit non-technical personnel to carry out these analyses.

It is known, in Pilloni et al, Anal. Chim. Acta, 35 (1966) pages 325–329, to produce complex colored products by reacting diethyllead ion with the monosodium salt of 4-(2-pyridylazo)-resorcinol. This reaction is carried out in a buffered solution and a pH of about 9. The ions were produced from diethyllead dichloride. Also, similar disclosure is made by Dagnall et al in Talanta, Vol. 12 (1965) pages 583–588. Reference is also made to the text of Shapiro and Frey, The Organic Compounds of Lead, John Wiley & Sons, New York (1968), in particular, pages 75, 77, 266 and 302, which mentions organolead salts and the reaction with chelates.

None of the aforesaid references discloses a single, rapid yet exact method of determining a range of concentrations of lead in trace amounts in gasoline.

U.S. application Ser. No. 371,338, filed on June 18, 1973 discloses and claims a method of rapid trace lead analysis for unleaded gasoline by forming lead iodides. The method described in the said copending application is very accurate, providing that the source of the lead is known. However, commercial lead alkyl mixtures contain various concentrations of the tetramethyllead, which is relatively slower to form halides. Thus, if the lead source were not known, some of the tetramethyllead content of the gasoline may not have been susceptible to analysis by the said process.

SUMMARY OF THE INVENTION

In the present invention, the trace lead content of gasolines may be colorimetrically analyzed, regardless of the source of the lead, by the steps of converting the organolead compounds therein to the iodide by reacting them with iodine in organic solvent in the presence of a tetraalkylammonium halide and subjecting the resulting mixture to ultra-violet radiation or heat, shaking the reaction mixture with an aqueous inorganic acidic compound which does not react with the colorimetric reagent of the succeeding step, separating the resulting aqueous phase from the gasoline organic phase and passing the aqueous phase into an aqueous solution of a di-alkali metal salt of 4-(2-pyridylazo)-resorcinol to produce a color therein which relates to the lead content of the gasoline. The method of this invention is applicable to all commercially used lead alkyls and to inorganic lead compounds (lead sulfate) regardless of the differences of proportions of the various lead compounds.

DESCRIPTION OF SPECIFIC EMBODIMENTS

Present governmental specifications limit the maximum lead content in automotive gasolines to 0.05 grams per gallon. This level may be changed by future governmental restrictions. By the simple steps of this invention commercial gasolines containing lead may be analyzed quickly. Gasoline formulations containing lead from tetramethyllead (TML), tetraethyllead (TEL), reaction mixes 25, 50, and 75, of TML and TEL, physical mixes of TML and TEL, or inorganic lead can be measured by this method. The distribution of compounds in the reaction mixes are typically as follows:

|       | Reaction Mix 25 | Reaction Mix 50 | Reaction Mix 75 |
|-------|-----------------|-----------------|-----------------|
| TML   | 0.4             | 5.7             | 30.0            |
| TMEL  | 4.3             | 23.8            | 42.2            |
| DMDEL | 20.1            | 37.5            | 22.1            |
| MTEL  | 42.2            | 26.2            | 5.2             |
| TEL   | 33.0            | 6.8             | 0.5             | wherein TMEL is trimethylethyllead, DMDEL is dimethyldiethyllead and MTEL is methyltriethyllead.

The desired halides in the analysis method of the aforementioned application U.S. Ser. No. 371,338 and in the present invention are the diiodides, to permit desired transfer of the halides to an aqueous substance in a short time and without loss. The sequence of reactions are understood to proceed as follows:

$$R_4Pb + I_2 \rightarrow R_3PbI + RI$$
$$R_3PbI + I_2 \rightarrow R_2PbI_2 + RI$$

The diorganolead diiodide is extracted into an aqueous phase and subsequently reacted to produce the color change. However, the lead compounds in the gasoline to be analyzed, i.e. tetramethyllead, tetraethyllead, trimethylethyllead, dimethyldiethyllead, methyltriethyllead or inorganic lead react at different rates. Tetramethyllead reacts to form halides relatively slowly and would require long reaction time or large excess amounts of halogen, e.g. iodine, for complete reaction. Otherwise, a portion of the initial lead content contributed by the TML may be lost in the analysis. On the other hand, using excess iodine, may cause interferences in subsequent complexes formed with colorimetric reagents.

Accordingly, to ensure substantially complete conversion of the organolead compounds to the di-iodide in this invention, the gasoline sample is mixed with iodine in an organic solvent in the presence of a tetraorganoammonium halide of the formula

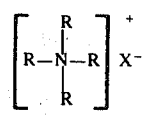

wherein the R groups are organic groups, preferably alkyl, aryl, alkaryl and aralkyl of 1 to 20 carbon atoms, including methyl, ethyl, propyl, butyl, hexyl, cyclohexyl, octyl, decyl, dodecyl, hexadecyl, phenyl, tolyl, benzyl, phenylethyl and the like, and X is halogen: chlorine, iodine, fluorine, etc. Preferably, the R groups are alkyl or aralkyl, such as tetraethylammonium chloride, methyl-trihexylammonium chloride, methyltrioctylammonium chloride, methyltridecylammonium chloride, and the like. One of the preferred compounds of this invention is a mixed-alkyl methylammonium chloride referred to as methyltricaprylylammonium chloride, wherein three of the R groups is a mixture of 8 and 10 carbon alkyls, predominantly $C_8$, ("Aliquat 336," a product of General Mills Chemicals, Inc.). It is believed that the tetraorganoammonium halide is essential for the conversion of all organolead compounds in the gasoline to water soluble iodides in the desired reaction time using a stoichiometric amount of iodine. Sufficient amount of iodine is added to react with the upper level concentration range of lead under consideration. While 0.1 gram of lead compound per gallon of sample is a presently satisfactory maximum, higher levels, even up to 1.0, may be employed in the present method.

The organic solvent used in this step may be a hydrocarbon, aromatic or alkane, a halogen-containing solvent, or an alcohol. Benzene, toluene, $C_6$ to $C_{16}$ alkanes, such as octane, decane or cyclohexane, halogenated hydrocarbons of 1 to 10 carbon atoms such as chloroform, methylene dichloride, ethylene dichloride, and alcohols, such as methanol, isopropanol, octanol, etc., may be used. The resulting mixture is then exposed to ultra-violet radiation, such as 3660 A wavelength, or heat. The U.V. exposure or heating is carried out for a time sufficient to convert the tetraorganolead compounds to dialkyllead diiodide. This time period may range from about 30 seconds to about 10 minutes, and usually from 1 minute to about 6 minutes. In the preferred procedure, a sample of about 2 to 5 ml of gasoline may be exposed to U.V. radiation for about 3 minutes. Alternatively, the mixture may be heated, preferably at from 75° to 150°C. for the said period of time. For example, placing a container of the sample in boiling water for from 1 to 6 minutes provides a satisfactory treating step.

Following this exposure, the test sample is removed from the U.V. or heat source and mixed with an aqueous solution of an acidic material which will not interfere with the colorimetric response in the subsequent step, preferably ammonium nitrate or nitric acid in water. This mixing produces a two phase mixture of gasoline and water, in which the pH is in the range of 4.0 to about 6.0. The concentration of the ammonium nitrate solution may be from about 5 grams to about 30 grams of $NH_4NO_3$ per liter of solution, and preferably from 10 to about 20 g/l. The concentration of the nitric acid is about 0.1 Normal. The two solutions may be mixed by shaking manually or by mechanical agitation. The di-iodides are understood to enter the water phase. Also, any inorganic lead compounds present in the sample, such as lead sulfate present as contaminants also enter the water phase and participate in the subsequent colorimetric analysis.

The aqueous phase is separated from the gasoline phase. This separation may be carried out by decanting, by filtering the mixed solutions or any other physical means. In a filtration step, the aqueous phase passes through the filter element first and the organic layer is discarded. The aqueous phase is then mixed with an aqueous solution of a di-alkali metal salt of 4-(2-pyridylazo)-resorcinol (PAR) the preferred salt being the disodium salt, hereinafter also referred to as PAR-Na. The di-iodide and inorganic lead compounds, which may be in the form of iodides, react with the PAR salt to produce a colorimetric change which corresponds to the lead concentration in the gasoline sample. In the preferred embodiment PAR-Na is used in an aqueous solution containing from about 10 mg to about 30 mg PAR-Na per liter and a sufficient amount of ammonium hydroxide to increase the pH of the resulting aqueous mixture to 6 to 10. Other useful alkali metal salts of PAR include dipotassium-PAR and dilithium-PAR.

Upon achieving the colorimetric change in the PAR-Na phase, the resulting mixture may be evaluated either by a colorimeter or by visually comparing the color obtained with a set of color standards equivalent to the lead concentration. By standardizing the amounts and the concentrations of gasoline and reagents used in each step, the only variable would be the resulting color in the final phase from which one may determine the lead concentration of the gasoline sample. The test results are in grams of lead per gallon of gasoline (g Pb/gal). Test method results over the range 0.00 to 0.10 g Pb/gal obtained using a colorimeter, agree within ± 0.005 g Pb/gal with those obtained by the atomic absorption technique, ASTM D-3237 which is the accepted reference test for trace lead in gasoline as published in the Federal Register. Test method results obtained using the visual comparison standards over the range 0.00 to 0.04 g Pb/gal agree within ±0.01 g Pb/gal with those obtained by that same ASTM D-3237 method; those samples containing between 0.04 and 0.10 g Pb/gal are reported as being suspect and possibly containing lead greater than the 0.05 g/gal limit, in the visual comparison technique.

In order to relate lead concentrations to the absorbances of a colorimeter or to colors of comparison materials, gasolines of known lead concentrations must be prepared and treated by the method of this invention. The preferred wavelength of measurement on a colorimeter is 514 nm. However any colorimeter capable of measurement near 514 nm is acceptable.

The following detailed procedure illustrates one manner of carrying out the method of this invention:

Step 1: 2 ml of gasoline sample is put into a one-ounce glass vial (1 inch diameter and 1/16 inch wall thickness);

Step 2: 2 ml of solution prepared by dissolving about 1 gram of iodine and about 1 gram of tetraethylammonium chloride in 100 ml of chloroform is added to the tube;

or Step 2': 2 ml of a solution prepared by dissolving 1 gram of iodine and 1 ml of methyltricaprylylammonium chloride in 100 ml of octanol;

Step 3: the vial is capped and subjected to U.V. light for 3 minutes;

or Step 3': the vial is placed in a boiling water bath for 5 minutes;

Step 4: 10 ml of a solution of ammonium nitrate, prepared by dissolving 15 g of ammonium nitrate in a liter of water, is added to the vial and the mixture is shaken for one minute;

or Step 4': 10 ml of 0.1N $HNO_3$ is added to the vial, and the mixture is shaken;

Step 5: 5 ml of a PAR-Na solution, prepared by dissolving 25 mg of PAR-Na and 10 ml of concentrated ammonium hydroxide in a liter of water, is put into a clean tube (18 × 150 mm) and a funnel with filter paper is then placed in the tube;

Step 6: The contents of the vial are allowed to settle into two phases and then poured together into the funnel; the aqueous phase will pass through the paper first while only a negligible amount of the organic layer goes through;

Step 7: The funnel is removed from the tube when the aqueous phase passes through and the tube contents are swirled until the resulting color is uniform throughout the tube;

Step 8: The color is evaluated by either placing the tube in a colorimeter and measuring the absorbance or by comparing the color so obtained with a series of standard color tubes corresponding to lead concentration.

Gasoline samples of known lead content were used to calibrate a colorimeter (Model T-600 of F & J Scientific, with 490 nanometer filter). The zero absorbance is set using water in the tube. Then the various samples prepared by the above steps were analyzed. The following results were obtained:

| Lead Content of Gasoline, g Pb/gal. | Absorbance At 490 nm. |
|---|---|
| 0.0 | 0.140 |
| 0.01 | 0.220 |
| 0.02 | 0.285 |
| 0.03 | 0.385 |
| 0.04 | 0.455 |
| 0.05 | 0.530 |
| 0.06 | 0.590 |
| 0.07 | 0.650 |
| 0.08 | 0.750 |
| 0.09 | 0.850 |
| 0.10 | 0.907 |

A straight-line curve prepared from these data provides a means of analyzing an unknown sample. It should be noted that these figures are one set of typical absorbance values; each colorimeter would give a slightly different reading and each one is therefore calibrated separately.

Alternatively, the color of the PAR-Na-water phase may be visually compared with standard color solutions. The color of the said phase corresponds to the lead concentration as follows:

| Lead Content g Pb/gal. | PAR-Na-Water Phase Color |
|---|---|
| 0.00 – 0.02 | Yellow |
| 0.03 – 0.04 | Yellow-orange |
| 0.05 – 0.06 | Orange |
| 0.07 – 0.10 | Orange-red |
| Over 0.10 | Red |

Thus any gasoline may be analyzed, whether free of lead content or containing high amounts of lead, that is even over 0.10 g/gal.

The color standards may be prepared from any source, color papers or cards or plastic surfaces ranging from yellow to red. Also, water solutions of pigments, preferably inorganic because of cost, may be prepared. The two stock solutions used in U.S. Ser. No. 371,338 of potassium dichromate and cobaltic chloride hexahydrate are useful in this instance. The yellow $K_2Cr_2O_7$ solution is prepared by dissolving 122.6 mg $K_2Cr_2O_7$ in 75 ml of water, then diluted to 100 ml with water. The red $CoCl_2.6H_2O$ solution is prepared by dissolving 5 g of $CoCl_2.6H_2O$ in 75 ml of an aqueous hydrochloric acid solution (10 ml concentrated HCl in 1 liter of water solution), then diluted to 100 ml with hydrochloric acid solution. These two stock solutions may be mixed as follows:

| Lead Content, g Pb/gal. | $CoCl_2.6H_2O$ ml | $K_2Cr_2O_7$ ml | Water, ml |
|---|---|---|---|
| 0.01 | 2.0 | 5.0 | 10.0 |
| 0.02 | 5.0 | 5.0 | 10.0 |
| 0.04 | 10.0 | 5.0 | 15.0 |

Using the method of this invention, these color standard solutions may be used for all gasolines, including those containing lead as TML, TEL, their reaction and physical mixes and inorganic lead. In the case of governmental restrictions on a maximum lead content, such as 0.05 g/gal, if the sample matched the 0.01, 0.02, or 0.04 g/gal standard reference colors, the sample would be considered to meet that restriction. If the sample was a darker orange than the 0.04 g/gal standard or a definite red color, it could be returned to a laboratory for quantitative lead analysis by ASTM D-3237.

The equipment necessary to carry out the steps of this invention may be provided in a convenient field test kit in which the vials and tubes have marked levels for the several additions, and premixed reagent solutions. A small colorimeter or set of color standards as well as pipettes and other measuring devices may be included. The U.V. light source, with sufficient guards can be fitted into the kit. Of great value in this invention is the convenience in permitting service station attendants, terminal and refinery workers and others not necessarily skilled in laboratory procedure to carry out the steps.

Having described this invention, I claim:

1. A method for colorimetrically determining the lead content in gasoline comprising (1) mixing a gasoline sample containing tetraalkyllead with iodine in the presence of a tetraorganoammonium halide and exposing the mixture to ultra-violet radiation from a 3660 A wavelength ultra-violet source for a period of from 30 seconds to about 10 minutes sufficient to convert the tetraalkyllead to dialkyllead diiodide, (2) mixing the resulting reaction mixture with an aqueous solution of an acidic compound selected from the group consisting of nitric acid and ammonium nitrate and separating the resulting aqueous phase from the organic gasoline phase, and (3) combining the aqueous phase with an alkali metal salt of 4-(2-pyridylazo)-resorcinol in an aqueous solution to produce a color corresponding to the initial lead concentration.

2. The method of claim 1 wherein the separation of the aqueous phase in Step 2 is carried out by filtering the combined aqueous and organic phases, whereby the aqueous phase passes through the filter first and directly into the said aqueous solution containing the alkali metal salt.

3. The method of claim 1 wherein the said alkali metal salt is disodium 4-(2-pyridylazo)-resorcinol.

4. The method of claim 1 wherein the tetraorganoammonium halide has the formula

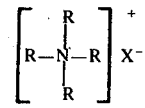

wherein the R groups are individually selected from the group consisting of alkyl, aryl, aralkyl and alkaryl of from 1 to 20 carbon atoms and X is a halide.

5. The method of claim 4 wherein the R groups are alkyl.

6. The method of claim 5 wherein the four R groups are ethyl and X is chlorine.

7. The method of claim 1 wherein the tetraorganoammonium halide is methyltricaprylyl ammonium chloride.

8. A method for colorimetrically determining the lead content in gasoline comprising (1) mixing a gasoline sample containing from 0 to over 0.10 grams of a tetraalkyllead compound per gallon of gasoline with iodine in the presence of a tetraorganoammonium halide and exposing the mixture to ultra-violet radiation from a 3660 A wavelength ultra-violet source for a period of from 30 seconds to about 10 minutes sufficient to convert the tetraalkyllead to dialkyllead diiodide, (2) mixing the resulting reaction mixture with an aqueous solution of an acidic compound selected from the group consisting of nitric acid and ammonium nitrate and separating the resulting aqueous phase from the organic gasoline phase, and (3) combining the aqueous phase with an alkali metal salt of 4-(2-pyridylazo)-resorcinol in an aqueous solution to produce a color corresponding to the initial lead concentration.

9. The method of claim 8 wherein the tetraalkyllead compounds are derived from lead alkyl formulations for gasoline selected from the group consisting of tetramethyllead, tetraethyllead, trimethylethyllead, dimethyldiethyllead and methyltriethyllead.

* * * * *